United States Patent [19]
Chan et al.

[11] Patent Number: 5,651,960
[45] Date of Patent: Jul. 29, 1997

[54] METHOD AND COMPOSITION FOR REMOVING SEMI-PERMANENT COLOR FROM HUMAN HAIR

[75] Inventors: Alexander C. Chan, Buffalo Grove; Fe P. Pascual, Elk Grove, both of Ill.

[73] Assignee: Helene Curtis, Inc., Chicago, Ill.

[21] Appl. No.: 532,252

[22] Filed: Sep. 22, 1995

[51] Int. Cl.$^6$ .................. A61K 7/13; A61K 7/135
[52] U.S. Cl. .................. 424/70.6; 424/62; 8/405; 132/208
[58] Field of Search .................. 424/70.6, 62; 8/405; 132/208

[56] References Cited

U.S. PATENT DOCUMENTS

| | | | |
|---|---|---|---|
| 3,616,803 | 11/1971 | Menkart et al. | 132/7 |
| 3,892,845 | 7/1975 | Cunningham | 424/62 |

FOREIGN PATENT DOCUMENTS

| | | |
|---|---|---|
| 49081548 | 8/1974 | Japan . |
| 4356413 | 12/1992 | Japan . |

OTHER PUBLICATIONS

Zviak, *The Science of Hair Care*, 1986 pp. 195–198.

Primary Examiner—Salle M. Gardner
Attorney, Agent, or Firm—Milton L. Honig

[57] ABSTRACT

The invention is an aqueous composition for removing coloring from hair treated with semipermanent hair colorant. The composition includes a reducing agent, at least one alcohol, water and an alkaline compound. A sufficient amount of the alkaline compound is employed to maintain the pH of the composition in the range of about 9.0 to about 11.0. The invention also includes a method of removing, or bleaching, colorant from semipermanent colored hair. The method includes applying the aqueous composition to semipermanently colored hair producing bleached hair. Lastly, the bleached hair is rinsed and shampooed.

10 Claims, 1 Drawing Sheet

METHOD AND COMPOSITION FOR REMOVING SEMI-PERMANENT COLOR FROM HUMAN HAIR

FIELD OF THE INVENTION

The invention relates generally to hair care products, and specifically to such products intended for use in removing hair coloring.

BACKGROUND OF THE INVENTION

While hair coloring becomes more popular in the consumer market, satisfactory coloring is difficult to achieve. For that reason, some users of coloring products prefer semi-permanent hair coloring instead of permanent hair coloring products. One benefit of semi-permanent over permanent hair coloring products is that semi-permanent coloring (which usually utilizes nitro dyes, azo dyes, anthroquinone dyes, etc.) can be removed by shampooing the hair 6–8 times. Sometimes, a user would want to remove the semi-permanent coloring sooner than the number of shampoos required because of an unsatisfactory or the undesirable resultant hair color. At present, no convenient and efficient method of, and product for, removing semi-permanent coloring from hair is available or known.

It is commonly known that natural hair color can be stripped and bleached with peroxide-based compositions. Such products, however, damage hair and fail to strip or bleach semi-permanent coloring from treated hair.

In DE 2,024,799, it is taught to use an aqueous mixture of alcohol and inorganic salt to remove type D and C dyes from hair. That method, however, also fails to remove semi-permanent coloring from hair.

A mixture of a sulfite, an alcohol and a cationic surfactant is disclosed in JP 4-356413 for removing color from hair at a pH of 7.0 to 9.0. Although that composition is slightly superior to the composition disclosed in DE 2,024,799 in terms of removing semi-permanent coloring from hair, its performance is still unsatisfactory.

Stripping and bleaching compositions containing a reducing agent and a chelating agent for skin are disclosed and claimed in JP 49-081548. That patent teaches the use of reducing agents, such as thioglycolic acid and its salts, at a pH of 5–9 to remove stains from skin. Such stains occurred during the coloring process. That composition does not efficiently or effectively remove semi-permanent coloring from hair as demonstrated by the examples herein below.

As a result, there exists a long-felt need for a new bleaching or stripping solution that overcomes such inefficiencies. There also exists a need for a bleaching product that can be used in the professional salon trade market and for home use via the consumer market.

The present invention overcomes these and other disadvantages of prior hair bleaching and stripping products. One object of the invention is the superior removal of more colorant and dye from hair colored with semi-permanent dyes. As a result, the user can achieve satisfactory coloring with less trial-and-error and in less time.

SUMMARY OF THE INVENTION

In contrast, conventional semipermanent coloring products are generally known as requiring between 6–8 shampoo treatments to remove the coloring. One aspect of the present invention is an aqueous composition for removing coloring from semipermanent color-treated hair in one treatment. The present composition must include a reducing agent capable of reducing sulfur atoms in human hair, at least one alcohol, water and an alkaline compound. A sufficient amount of an alkaline compound is employed to render or maintain the pH of the composition in the range of about 8.0 to about 11.0.

Another aspect of the present invention is a method of removing coloring, or dye, from semipermanent color-treated hair. The method includes the steps of first providing an aqueous composition comprising a reducing agent capable of reducing sulfur in human hair, at least one alcohol, water and an alkaline compound in an amount sufficient to maintain the pH of the composition in the range of about 8.0 to about 11.0. Next, semipermanent color-treated hair is provided having a predetermined concentration of dye or colorant adhered to or within the hair. Next, the aqueous composition is applied to the color-treated hair producing a color-stripped hair. Lastly, the color-stripped hair is rinsed and/or shampooed after a waiting time sufficient to remove at least a portion of the dye or colorant from the hair. As a result, that treated hair is de-colored.

DETAILED DESCRIPTION OF THE INVENTION

Figure 1:
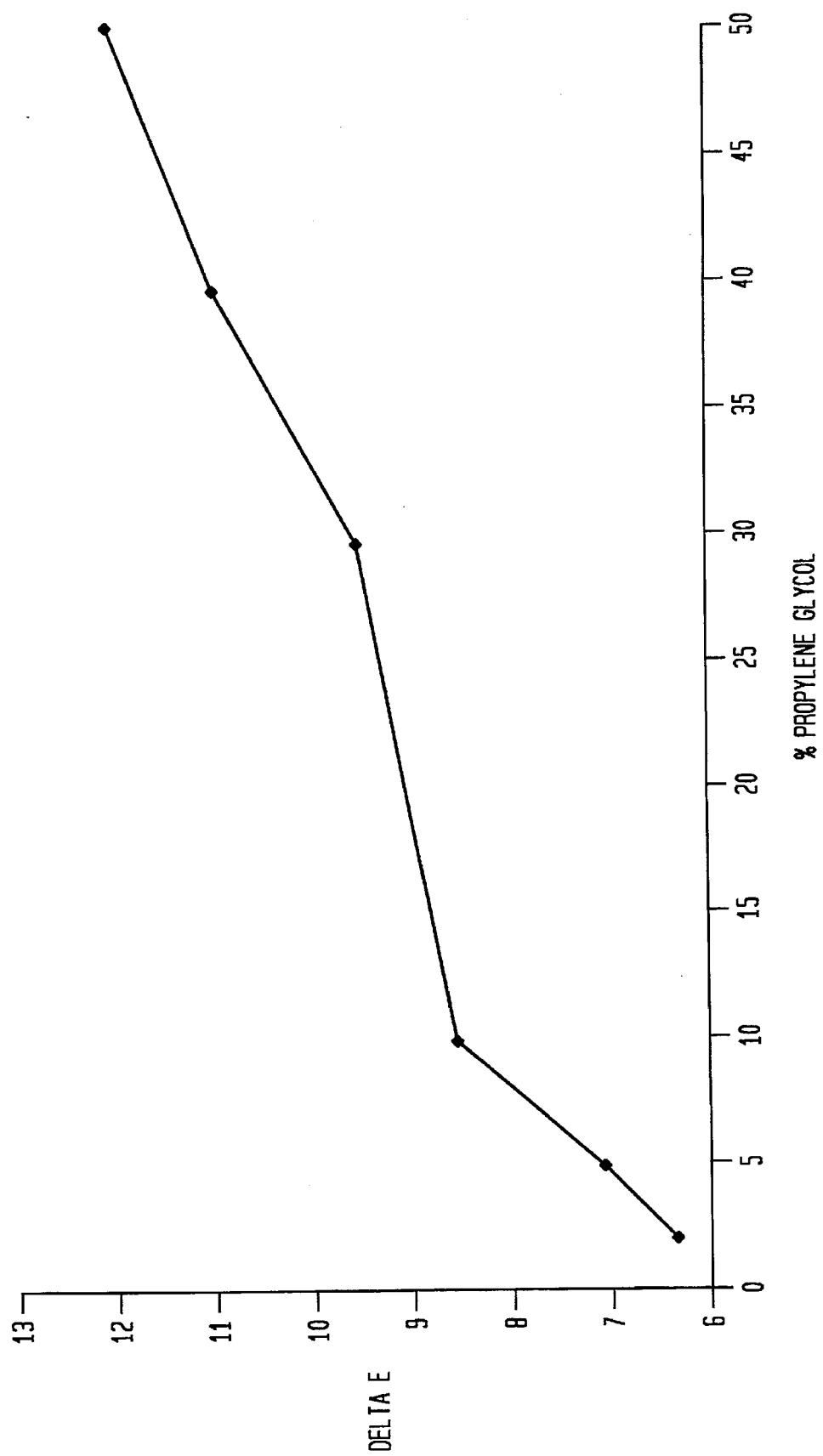
FIG. 1 is a graph of $\Delta E$ vs. the weight percent content of propylene glycol, which illustrates how the inclusion of polyhydroxy-containing aliphatic compounds would adversely affect the present invention.

The reducing agent of the present invention is an organic compound containing at least one mercapto group (—SH). In the art, mercapto groups are also referred to as thiols and sulfhydryl groups, or moieties. Preferably, the reducing agent is an aliphatic compound such as thioglycolic acid (also known as mercaptoacetic acid), a salt of thioglycolic acid, 2-mercaptopropionic acid, a salt of 2-mercaptopropionic acid, β-mercaptopropionic acid, a salt of β-mercaptopropionic acid, 2-mercaptoethanol acid, 3-mercapto-1,2-propanediol, 1,3-dimercapto-2-propanol, 1,4-dimercapto-2-butanol, 1,3-dimercapto-2-methoxypropane, 1,3-dimercapto-2-aminopropane, 1,4-dimercapto-2,3-diaminobutane, glycerol monomercaptoacetate, cysteamine HCl or combinations and mixtures thereof. More preferably, the reducing agent is a thioglycolic acid or its salt, or cysteamine HCl.

In the composition of the present invention, the concentration of the reducing agent is sufficient to bleach the semi-permanent color adhered to or within the hair. Preferably, the concentration of the reducing agent is in the range of 0.1 to 10.0% by weight of the total weight of the composition. More preferably, the reducing agent is present in the range of 1.0 to 4.0% by weight of the composition.

An alcohol capable of wetting human hair is also included in the composition of the present invention. By "wetting" it is meant that the alcohol functions to wet the hair enhancing removal of semi-permanent coloring. The alcohol also acts as a swelling agent that enhances the penetration of the reducing agent, and thus the color stripping process.

Preferably, the alcohol is a $C_{1-6}$ alcohol having a straight or branched chain. More preferably, the alcohol is ethyl alcohol, isopropyl alcohol, benzyl alcohol, substituted alcohol, or mixtures and combination thereof.

In the composition, the alcohol is present in a concentration sufficient to wet and/or swell human hair so that the composition effectively removes semipermanent hair coloring. Preferably, the concentration of the alcohol is in the range of 0.1 to 25% by weight of the composition. More preferably, the alcohol comprises in the range of 1.0 to 10.0% by weight of the composition.

In the preferred embodiment, the alkaline compound of the invention is ammonium hydroxide. The alkaline compound is employed in an amount or concentration sufficient to maintain the pH of the composition in the range of about 8.0 to 11.0. Preferably, the pH is maintained in the range of about 9.0 to 10.0.

Optional ingredients may also be included. For example, a soap, such as sodium lauryl sulfate or sodium stearyl sulfate may be employed to enhance color removal. Other adjuvants, or optional ingredients, include conventional solvents, conditioners, surfactants, alkalizing agent, buffers, thickeners, fragrances, other conventional adjuvants, any compatible combination thereof. Such adjuvants are employed to impart known desirable results and properties depending upon a desired form of the total composition. Preferably, the water is deionized.

The method of the invention may further include the step of shampooing the color-stripped hair or the de-colored hair.

EXAMPLES

Example 1

Solutions A and B of the present invention were prepared by mixing the ingredients. The make-up of Solutions A and B are as follows.

Solution A includes 3.35 grams of a 75% by weight solution of Cysteamine HCl in water, 15.0 grams of a 30% by weight solution of sodium lauryl sulfate in water, and 5.0 grams benzyl alcohol. The final weight of the composition was adjusted to 100 grams by adding deionized water. The pH was adjusted to 9.67 by adding concentrated ammonium hydroxide solution.

Solution B included 4.0 grams of a 60% by weight solution of ammonium thioglycolate in water, 15.0 grams of a 30% by weight solution of sodium lauryl sulfate in water, and 5.0 grams benzyl alcohol. The final weight of the composition was adjusted to 100 grams by adding deionized water q.s. The pH was adjusted to 9.04 by adding concentrated ammonium hydroxide solution.

For comparative purposes, Solution C is a replication of the hair dye removing composition used in JP 4-356413 assigned to Hoyu. Solution C includes 4.0 grams of sodium sulfite ($Na_2SO_3$), 3.0 grams of cetylammonium chloride, and 5.0 grams of benzyl alcohol. The final solution was adjusted to 100 grams by adding deionized water q.s. The pH of the resultant solution was 9.98.

Shown in Table 1 is a comparison between Solutions A and B of the present invention and Solution C used in Hoyu. Light brown hair tresses were dyed with Disperse Violet #1. Disperse Violet #1 is a hair dye composition containing 0.15 grams of Disperse Violet #1 dye, 1.8 grams of ethyl alcohol, and 11.05 grams of a 1% by weight aqueous solution of hydroxyethylcellulose. The pH of the solution was 9.77.

Individual colored tresses were treated with Solutions A, B and C, respectively, for 20 minutes. All chromaticity values (L, a, b) were taken using a Chroma-sensor CS-5 system available from Applied Color Systems, Inc. located in Lawrenceville, N.J. The symbol "$\Delta E$" represents the total change in value of the chromaticity from the original natural blonde tress. The symbol "$\Delta L$" represents the change in the L value upon the indicated treatment. The symbols "$\Delta a$" and "$\Delta b$" represent the change in the a and b values upon the indicated treatment. As the value of $\Delta E$ decreases, the degree of color removal from the colored tresses increases. As shown in Table 1, the present invention is superior to Solution C.

TABLE 1

|  | L | a | b | $\Delta E^*$ |
|---|---|---|---|---|
| Untreated, light brown hair tress | 30.0 | 4.7 | 8.0 |  |
| Hair colored with semi-permanent colorant[1] | 27.8 | 4.9 | 6.4 | 2.7 |
| Colored hair[1] treated with cysteamine HCl (Solution A) | 30.0 | 4.6 | 7.7 | 0.3 |
| Colored hair[1] treated with $NH_4$ thioglycolate (Solution B) | 29.2 | 4.8 | 7.7 | 0.9 |
| Colored hair[1] treated with $Na_2SO_3$ (Solution C) (JP 4-356413) | 29.4 | 4.4 | 5.8 | 2.3 |

[1]Tress dyed with Disperse Violet #1
*$\Delta E = [(\Delta L)^2 + (\Delta a)^2 + (\Delta b)^2]^{1/2}$ Example 2

Shown in Table 2 is a comparison between Solution B of the present invention and the solution disclosed in JP 4-356413 replicated as Solution C. The medium brown hair tresses were colored with HC Red #3. HC Red #3 is a hair dye composition containing 1.2 grams HC Red #3 dye, 10.7 grams of ethyl alcohol, 12.3 grams of cetyl alcohol, 40.8 grams of Standapol EA-1, and 35 grams of deionized water. That solution was adjusted to a pH of 9.6 by adding $NH_4OH$ q.s.

Individual colored tresses were treated with Solutions B and C, respectively, for 20 minutes, followed by a shampoo. As shown in Table 2, the present invention is superior to Solution C.

TABLE 2

|  | L | a | b | $\Delta E^*$ |
|---|---|---|---|---|
| Untreated, medium brown hair tress | 30.2 | 4.7 | 7.9 |  |
| Hair colored with semi-permanent colorant[2] | 21.3 | 8.0 | 4.0 | 10.3 |
| Colored hair[2] treated with $NH_4$ thioglycolate (solution B) and shampooed | 27.9 | 7.1 | 6.7 | 3.5 |
| Colored hair[2] treated with $Na_2SO_3$ (solution C), shampooed | 24.4 | 7.1 | 5.0 | 6.9 |

[2]Tress dyed with HC Red #3
*$\Delta E = [(\Delta L)^2 + (\Delta a)^2 + (\Delta b)^2]^{1/2}$ Example 3

Shown in Table 3 is another comparison between Solution B of the present invention and Solution C (JP 4-356413). Commercially bleached hair tresses were colored using HC Yellow #5. HC Yellow #5 is a hair dye composition containing 1.1 grams of HC Yellow #5 dye, 35.6 grams of ethyl alcohol, and 63.3 grams of deionized water. That solution was adjusted to a pH of 9.8 by adding $NH_4OH$ q.s.

Individual colored tresses were treated with Solutions B and C, respectively, for 20 minutes, followed by a shampoo. As shown in Table 3, the present invention is superior to Solution C.

TABLE 3

|  | L | a | b | $\Delta E^*$ |
|---|---|---|---|---|
| Untreated, commercially bleached hair tress | 62.8 | 3.1 | 13.9 |  |

TABLE 3-continued

|  | L | a | b | ΔE* |
|---|---|---|---|---|
| Hair colored with semi-permanent colorant[3] | 48.3 | 21.7 | 28.1 | 27.5 |
| Colored hair[3] treated with $NH_4$ thioglycolate (Solution B) and shampooed | 63.4 | 3.8 | 17.1 | 3.3 |
| Colored hair[3] treated with $Na_2SO_3$ (solution C) and shampooed | 57.6 | 6.5 | 24.2 | 12.0 |

[3]Tress dyed with HC Yellow #5
*ΔE = $[(\Delta L)^2 + (\Delta a)^2 + (\Delta b)^2]^{1/2}$

Example 4

For comparative purposes, Solution D was prepared to show criticality for the presence of an alcohol. Solution D included 5.0 grams of a 60% by weight solution of ammonium thioglycolate in water, and 15.0 grams of a 30% by weight solution of sodium lauryl sulfate in water. That solution was adjusted to 100 grams by adding deionized water q.s. and adjusted to a pH of 9.0 by adding concentrated ammonium hydroxide solution. Solution D contained no alcohol.

In accordance with the present invention, Solution E included 5.0 grams of a 60% by weight solution of ammonium thioglycolate in water, 15.0 grams of a 30% by weight solution of sodium lauryl sulfate in water, and 3.5 grams of isopropyl alcohol. That solution was adjusted to 100.0 grams by adding deionized water q.s. and adjusted to a pH of 9.0 by adding concentrated ammonium hydroxide solution.

Light brown hair tresses were dyed using HC Yellow #2. The HC Yellow #2 hair dye composition contains 0.1 grams of HC Yellow #2 dye, 1.0 grams of propylene glycol, 11.05 grams of a 1% solution by weight solution in water of hydroxyethylcellulose, and 0.5 grams of deionized water. The pH was 9.28.

Individual colored tresses were treated with Solutions D and E, respectively. The results in Table 4 show that the present of an alcohol enhances the removal of color.

The symbol "X" quantifies the degree to which color is stripped from the colored tress in relation to the original natural blonde tress. Higher "X" values indicates that the solution is stripping more color. The higher "X" values show that the invention effectively strips color from the colored tresses.

TABLE 4

|  | L | a | b | X* |
|---|---|---|---|---|
| Hair colored with semi-permanent colorant[4] | 28.3 | 6.9 | 11.6 | |
| Colored hair[4] treated with $NH_4$ Thioglycolate absent any alcohol (Solution D) | 29.3 | 4.9 | 9.6 | 2.8 |
| Hair colored with semi-permanent colorant[4] | 26.9 | 7.1 | 11.4 | |
| Colored hair[4] treated with $NH_4$ Thioglycolate including isopropyl alcohol (Solution E) | 29.0 | 4.8 | 9.2 | 3.2 |

[4]Light brown hair tress dyed with HC Yellow #2.
*X = $[(a_{treated} - a_{colored})^2 + (b_{treated} - b_{colored})^2]^{1/2}$

Example 5

Shown in Table 5 is another comparison between Solution D (alcohol-free) and Solution E of the present invention. The solutions are used to strip color from hair treated with a semi-permanent hair coloring product. Natural blonde hair tresses were colored using LOVING CARE™ shade #79, which is a semi-permanent hair coloring product manufactured by Clairol. Individual colored tresses were then treated with Solutions D and E, respectively, for 20 minutes. Superior stripping was obtained by Solution E of the present invention which contains an alcohol.

TABLE 5

|  | L | a | b | X* |
|---|---|---|---|---|
| Hair colored with semipermanent colorant[5] | 22.4 | 3.1 | 3.7 | |
| Colored hair[5] treated with $NH_4$ thioglycolate absent alcohol (Solution D) | 27.5 | 4.0 | 6.4 | 2.8 |
| Hair colored with semipermanent colorant[5] | 21.3 | 2.9 | 3.2 | |
| Colored hair[5] treated with $NH_4$ thioglycolate including isopropyl alcohol (Solution E) | 27.9 | 4.2 | 6.9 | 3.9 |

[5]Natural blonde hair tress dyed with LOVING CARE ™ shade #79 which is a semipermanent hair coloring product.
*X = $[(a_{treated} - a_{colored})^2 + (b_{treated} - b_{colored})^2]^{1/2}$

Example 6

Shown below in Table 6 is a comparison between Solution E of the present invention and the stain removal composition employed in German Patent No. DE 2024799 replicated as Solution F. Natural blonde hair tresses were colored with LOVING CARE™ shade #79, which is a semi-permanent hair coloring product manufactured by Clairol.

Solution F (DE 2024799) included 8.0 grams of isopropyl alcohol and 16.0 grams of solid sodium sulfate ($Na_2SO_4$), and 5.0 grams of a 28% by weight solution of ammonium hydroxide in water. That solution was adjusted to 100.0 grams by adding deionized water q.s.

The comparison in Table 6 shows that Solution E of the present invention is superior to the composition disclosed in DE 2024799 (Solution F).

TABLE 6

|  | L | a | b | X* |
|---|---|---|---|---|
| Hair colored with a semi-permanent colorant[6] | 21.3 | 2.9 | 3.2 | |
| Colored hair[6] treated with $NH_4$ thioglycolate including isopropyl alcohol (Solution E) | 27.9 | 4.2 | 6.9 | 3.9 |
| Hair colored with a semi-permanent hair colorant[6] | 21.0 | 2.5 | 2.2 | |
| Colored hair[6] treated with Solution F (DE 2,024,799) | 23.4 | 3.1 | 3.6 | 1.5 |

[6]Natural blonde hair tress dyed with LOVING CARE ™ shade #79 which is a semipermanent hair coloring product.
*X = $[(a_{treated} - a_{colored})^2 + (b_{treated} - b_{colored})^2]^{1/2}$

Example 7

Comparative Solution G was prepared at various concentrations of propylene glycol to show the effect of propylene glycol on the present invention. Solution G was prepared in the same manner as the present invention. Solution G was formulated by mixing, based on the total weight of the solution, a constant base of 5% by weight of a 38% by weight solution of ammonium thioglycolate in water; and 15% by weight of a 30% by weight solution of sodium lauryl sulfate. To that base, six (6) different concentrations of propylene glycol were added to obtain (6) six different solutions. Propylene glycol was employed at 2%, 5%, 10%, 30% 40%, and 50% by weight of the total weight of the solution. The remainder of each solution was deionized (D.I.) water. A 28% by weight solution of ammonium hydroxide q.s. was added to each solution to adjust the pH of each solution to 9.2.

In Example 7, natural blonde hair tresses were treated with Soft Toner Poly Color, Shade #63 manufactured by Henkel. The product is a semi-permanent hair coloring product. The dyed hair tresses were bleached with all six concentrations of solution G for 20 minutes and rinsed with water.

TABLE 7

| Weight percent propylene glycol | 2% | 5% | 10% | 30% | 40% | 50% |
|---|---|---|---|---|---|---|
| $\Delta E^*$ | 6.4 | 7.1 | 8.5 | 9.5 | 11.0 | 12.0 |

*$\Delta E = [(\Delta L)^2 + (\Delta a)^2 + (\Delta b)^2]^{1/2}$

The test data tabulated in Table 7 and graphed in FIG. 1 shows that the presence of propylene glycol causes a high $\Delta E$ value. In comparison to the alcohols used in the present invention, the presence of propylene glycol would adversely affect the $\Delta E$ value by increasing the value to undesirable levels. Increased $\Delta E$ directly corresponds to less color removal and less bleaching. Thus, propylene glycol is excluded from the present invention because it would impart deleterious effects.

In the art, it is known that glycerin may be used instead of propylene glycol as a thickener. In the context of the present invention, glycerin and other glycols and polyols known in the art have properties similar to propylene glycol. Therefore, glycerin, glycols and other polyols would adversely affect the $\Delta E$ value by increasing the value to undesirable levels. For that reason, such compounds are excluded from the present invention because it would impart deleterious effects.

While a particular embodiment of the present method and composition for removing color from human hair colored with semipermanent colorant has been described, it will be appreciated that changes and modifications may be made thereto without departing from the invention in its broader aspects and as set forth in the following claims.

What is claimed is:

1. A method of removing coloring from semipermanent color-treated hair comprising the steps of:
   providing a composition comprising a reducing agent which is an organic compound containing at least one mercapto group capable of reducing sulfur in human hair, at least one alcohol, water and an alkaline compound which is ammonium hydroxide in an amount sufficient to maintain the pH of the composition in the range of about 8.0 to about 11.0;
   providing semipermanent color-treated hair having a predetermined concentration of dye;
   applying the composition to the color-treated hair producing a color-stripped hair; and
   rinsing or shampooing the color-stripped hair after a time sufficient to remove a portion of the dye producing a de-colored hair.

2. The method of claim 1 wherein the reducing agent is a member selected from the group consisting of thioglycolic acid, a salt of thioglycolic acid, 2-mercaptopropionic acid, a salt of 2-mercaptopropionic acid, β-mercaptopropionic acid, a salt of β-mercaptopropionic acid, 2-mercaptoethanol, 3-mercapto-1,2-propanediol, 1,3-dimercapto-2-propanol, 1,4-dimercapto-2-butanol, 1,3-dimercapto-2-methoxypropane, 1,3-dimercapto-2-aminopropane, 1,4-dimercapto-2,3-diaminobutane, glycerol monomercaptoacetate, cysteamine, an acid salt of cysteamine and combinations thereof.

3. The method of claim 2 wherein the reducing agent is an ammonium salt of thioglycolic acid or cysteamine HCl salt.

4. The method of claim 1 wherein the reducing agent comprises in the range of 0.1 to 10.0% by weight of the composition and the alcohol comprises in the range of 0.1 to 25% by weight of the composition.

5. The method of claim 1 wherein the reducing agent comprises in the range of 1.0 to 4.0% by weight of the composition and the alcohol comprises in the range of 1.0 to 10.0% by weight of the composition.

6. The method of claim 1 wherein the alcohol is an alcohol having a $C_{1-6}$ straight or branched chain, or combinations thereof.

7. The method of claim 1 wherein the alcohol is selected from the group consisting of ethyl alcohol, isopropyl alcohol, benzyl alcohol, hexyl alcohol and combinations thereof.

8. The method of claim 1 wherein the composition further includes a soap, a solvent, a conditioner, a surfactant, a thickener, an alkalizing agent, a fragrance, a buffer, or a combination thereof compatible with the reducing agent.

9. The method of claim 8 wherein the soap is sodium lauryl sulfate or sodium stearyl sulfate, the water is deionized, and the alkaline compound is a solution of ammonium hydroxide in an amount sufficient to maintain the pH of the composition in the range of about 9.0 to about 10.0.

10. A method of removing coloring from semipermanent color-treated hair comprising the steps of:
   providing a composition comprising thioglycolic acid or a salt thereof, at least one alcohol, sodium lauryl sulfate or sodium stearyl sulfate, deionized water and an alkaline compound which is ammonium hydroxide in an amount sufficient to maintain the pH of the composition in the range of about 9.0 to about 10.0;
   providing semipermanent color-treated hair having a predetermined concentration of dye;
   applying the composition to the color-treated hair producing a color-stripped hair; and
   shampooing the color-stripped hair after a time sufficient to remove a portion of the dye producing a de-colored hair; and,
   rinsing the de-colored hair with water.

* * * * *